(12) United States Patent  (10) Patent No.: US 9,364,604 B2
Ferrarini et al.  (45) Date of Patent: Jun. 14, 2016

(54) EXTRACORPOREAL BLOOD TREATMENT MACHINE

(75) Inventors: Lorenza Ferrarini, Medolla (IT); Danielle Pelletier, Sainte-Foy les Lyon (FR); Massimo Zaccarelli, San Felice sul Panaro (IT); Jeffrey J. Letteri, Punta Gorda, FL (US)

(73) Assignee: Gambro Lundia AB, Lund (SE)

( * ) Notice: Subject to any disclaimer, the term of this patent is extended or adjusted under 35 U.S.C. 154(b) by 934 days.

(21) Appl. No.: 13/162,913

(22) Filed: Jun. 17, 2011

(65) Prior Publication Data

US 2011/0240537 A1  Oct. 6, 2011

Related U.S. Application Data

(63) Continuation of application No. 10/948,703, filed on Sep. 24, 2004, now abandoned.

(60) Provisional application No. 60/532,566, filed on Dec. 29, 2003.

(30) Foreign Application Priority Data

Sep. 25, 2003 (IT) .............................. MO2003A0259

(51) Int. Cl.
   *G06F 3/01*   (2006.01)
   *A61M 1/36*   (2006.01)
   *G06F 19/00*  (2011.01)

(52) U.S. Cl.
   CPC ........... *A61M 1/367* (2013.01); *G06F 19/3406* (2013.01); *A61M 2205/12* (2013.01); *A61M 2205/505* (2013.01)

(58) Field of Classification Search
   USPC ................................................ 604/4.01, 5.01
   See application file for complete search history.

(56) References Cited

U.S. PATENT DOCUMENTS

| 5,326,476 | A | 7/1994 | Grogan et al. |
| 5,591,344 | A | 1/1997 | Kenley et al. |

(Continued)

FOREIGN PATENT DOCUMENTS

| EP | 0 655 004 B1 | 5/1995 |
| WO | WO 98/35747 | 8/1998 |
| WO | WO 02/26286 A2 | 9/2001 |
| WO | WO 02/26286 A3 | 4/2002 |

OTHER PUBLICATIONS

International Preliminary Report on Patentability for International Application No. PCT/IB2004/002929.

*Primary Examiner* — Anil N Kumar
(74) *Attorney, Agent, or Firm* — Mueting, Raasch & Gebhardt, P.A.

(57) ABSTRACT

A user interface for a machine for extracorporeal blood treatment comprises a touch screen and a controller programmed to display on a screen (16) a display in which two distinct areas are arranged, one of which (161) exhibits a series of touch keys (17). Activation of any one touch key (17) causes visualization of an image in a second area (162) of the screen. The images are displayed alternatively and are at least partly different one from another. Each touch key (17) is associated to an instruction, or to a group of instructions, all concerned with readying the machine for use. Each image is a pictograph of a configuration of the machine, correlated with an instruction associated to the touch key (17) selected. The operator is aided in making the machine ready for treatment.

11 Claims, 9 Drawing Sheets

(56) References Cited

U.S. PATENT DOCUMENTS

| | | |
|---|---|---|
| 5,679,245 A | 10/1997 | Manica |
| 6,361,518 B1 | 3/2002 | Brierton et al. |
| 7,033,539 B2 * | 4/2006 | Krensky et al. ............... 422/44 |
| 7,686,779 B1 * | 3/2010 | Gibbs ........................ 604/6.01 |
| 8,182,440 B2 * | 5/2012 | Cruz et al. ................... 604/4.01 |
| 2002/0085952 A1 * | 7/2002 | Ellingboe et al. .............. 422/45 |
| 2002/0151804 A1 | 10/2002 | O'Mahony et al. |
| 2003/0135152 A1 * | 7/2003 | Kollar et al. .................... 604/35 |

* cited by examiner

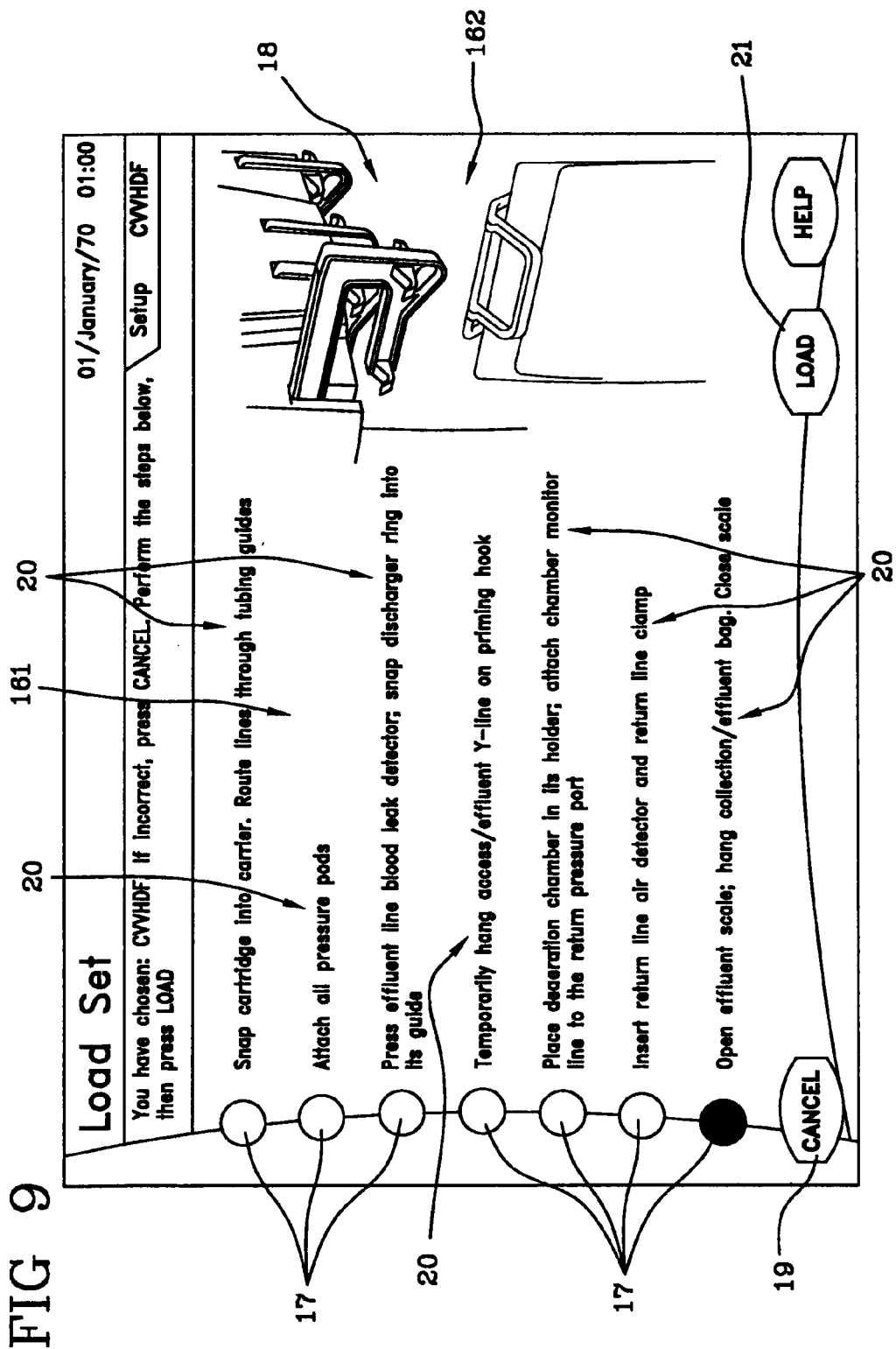

EXTRACORPOREAL BLOOD TREATMENT MACHINE

CROSS-REFERENCE TO RELATED APPLICATIONS

This application is a continuation of U.S. patent application Ser. No. 10/948,703, filed Sep. 24, 2004, now abandoned and claims the priority of Italian Patent Application No. MO2003A000259, filed on Sep. 25, 2033, and the benefit of U.S. Provisional Application No. 60/532,566, filed on Dec. 29, 2003, the contents of which are incorporated herein by reference.

BACKGROUND OF THE INVENTION

The invention relates to a user interface for a machine for extracorporeal blood treatment, as well as to a machine for extracorporeal blood treatment comprising the user interface.

Specifically, though not exclusively, the invention is usefully applied in the field of dialysis machines, such as for example machines for intensive treatment for acute renal failure.

In particular the invention relates to a user interface according to the preamble of the first claim.

Document WO 98/35747 teaches a dialysis machine, suitable for carrying out periodical dialysis treatments—including domestic treatment—which is provided with a user interface such as the one described in the preamble of the first claim, in which the user interface has a programmed controller that displays various layouts on a touch-screen monitor, in at least one of which layouts (FIG. 5) the screen is sub-divided into various areas. A first of these areas exhibits touch keys, each of which is associated to a parameter relating to the dialysis treatment; while in a second of the areas, following activation of any one of the touch keys in the first area, two further touch keys are displayed, each in the form of an arrow, through which the parameter selected by the first touch key (in the first area) can be modified (up or down).

In the second screen area at first a further touch key is displayed, dedicated in particular to the change of the drip chamber level in the extracorporeal circuit. Selection of this further touch key brings up an illustration of the drip chamber on-screen, and the user can indicate on the illustration the level present in the chamber at the time.

The touch screen further comprises other touch keys having various functions, such as for example, one key for returning to the previous display, another for viewing other data, another still for signalling problems, and so on.

The touch screen further comprises at least one other display (FIG. 4) with various touch keys; by activating this screen other user-processor dialog windows are opened.

User interfaces in dialysis machines generally have the function of setting up a dialog between the processor of the machine and the user or operator using the machine, for example in order to regulate machine operation or for setting desired treatment parameters, such as, for example, blood pump flow rate, the flow rate and temperature of the dialysis fluid, treatment times, and so on.

One of the aspects of user interfaces in known-type dialysis machines (for example WO 98/35747) which is liable to improvement is that relating to interaction between the user or operator and the machine during preparation procedures prior to the actual treatment.

Normally these readying procedures comprise at least the mounting of the disposable set onto the machine. The disposable set usually comprises at least the extracorporeal blood circuit, destined in use to be connected up to a vascular access of the patient about to undergo treatment, and the blood treatment unit, generally comprising a filtration unit (for example a dialyzer).

Treatment preparation procedures usually further comprise at least one priming stage for the circuit and the blood treatment unit, as well as a connection stage of the extracorporeal circuit to the vascular access of the patient.

These preparation procedures can be very long, complicated and laborious, especially with intensive therapy dialysis machines, where the machine operator is often not specialised in the use of these apparatus, and where the time factor is critical as the patient is often in quite a serious condition and needs as fast an intervention as possible.

SUMMARY OF THE INVENTION

An aim of the present invention is to provide a user interface which is able to improve setting-up time for the readying of an apparatus for extracorporeal blood treatment.

A further aim of the invention is to provide a machine for extracorporeal blood treatment in which the preliminary operations in preparation for a correct functioning of the machine are easy to do and immediate on the part of the user, even where the latter is not specialised.

An advantage of the invention is that it makes rapid learning possible, as well as rapid execution even by a non-expert user, of the procedural steps necessary for preparation of the machine for extracorporeal blood treatment.

A further advantage of the present invention is to provide a user interface which is easy to use, and by means of which times for carrying out the preliminary stages of machine preparation for extracorporeal blood treatment can be reduced—for example, in relation to the mounting of the single-use parts of the apparatus on the machine.

The aims and advantages and more besides are all achieved by the present invention, as it is characterised in one or more of the appended claims.

In a characteristic of the invention, the selection of any touch key located in a first area of a display will determine display, in a second area of the screen, of a corresponding image, each touch key being associated to a respective image.

In an embodiment of the invention, the images associated to the touch keys are shown in a different way, i.e. not at the same time in a second area of the display.

In an embodiment of the invention, the images displayed on the second area of the screen are, at least partially, different one from another.

In an embodiment of the invention, the user interface comprises a memory having a plurality of data (or data groups) which are displayed on the first area of the screen, each item (or group) of data being placed on-screen in a position in which it is visually associated to a respective touch-key.

In an embodiment of the invention, the above-cited data groups are displayed contemporaneously in the first area of the screen.

In an embodiment of the invention, the data groups are not cancelled if one of the touch keys is selected.

In an embodiment of the invention, the data groups comprise operating instructions for readying the machine.

In an embodiment of the invention, the images displayed in the second area of the screen comprise pictographs representing configurations of the machine correlated to instructions for operations to be performed on the machine itself.

In an embodiment of the invention, the contents of the data shown on the first area of the screen cannot be changed via the touch screen by a machine user.

In an embodiment of the invention, the data shown in the first area of the screen does not contain parameters which can be set by the operator.

In an embodiment of the invention, the second area of the screen is without touch keys, or other areas predisposed for data input, at least in the areas containing images associated to the touch keys in the first area.

In an embodiment of the invention, selecting a touch key determines a visible change in a part of the first area of the screen, being the part visibly associated on-screen with the selected touch key.

In an embodiment of the invention, a process for assisting an operator in readying the machine for extracorporeal blood treatment includes stages of: 1) bringing up on a touch-screen at least one display divided into at least two distinct areas, a first area exhibiting at least two touch keys, each touch key being associated to at least one instruction relating to readying the machine; 2) touching a touch key for selecting at least one operative instruction; 3) in response to the above selection, displaying a pictograph on a second area of the screen which represents a configuration of the machine which is correlated to the instruction given.

Further characteristics and advantages of the present invention will better emerge from the detailed description that follows, of at least one embodiment of the invention, illustrated by way of non-limiting example in the appended figures of the drawings.

BRIEF DESCRIPTION OF THE DRAWINGS

The description will be made with reference to the figures of the drawings, which are provided by way of non-limiting example, in which:

FIGS. 2 to 9 show user-interface displays which can be called on-screen in the machine of FIG. 1.

DETAILED DESCRIPTION

Figure 1:
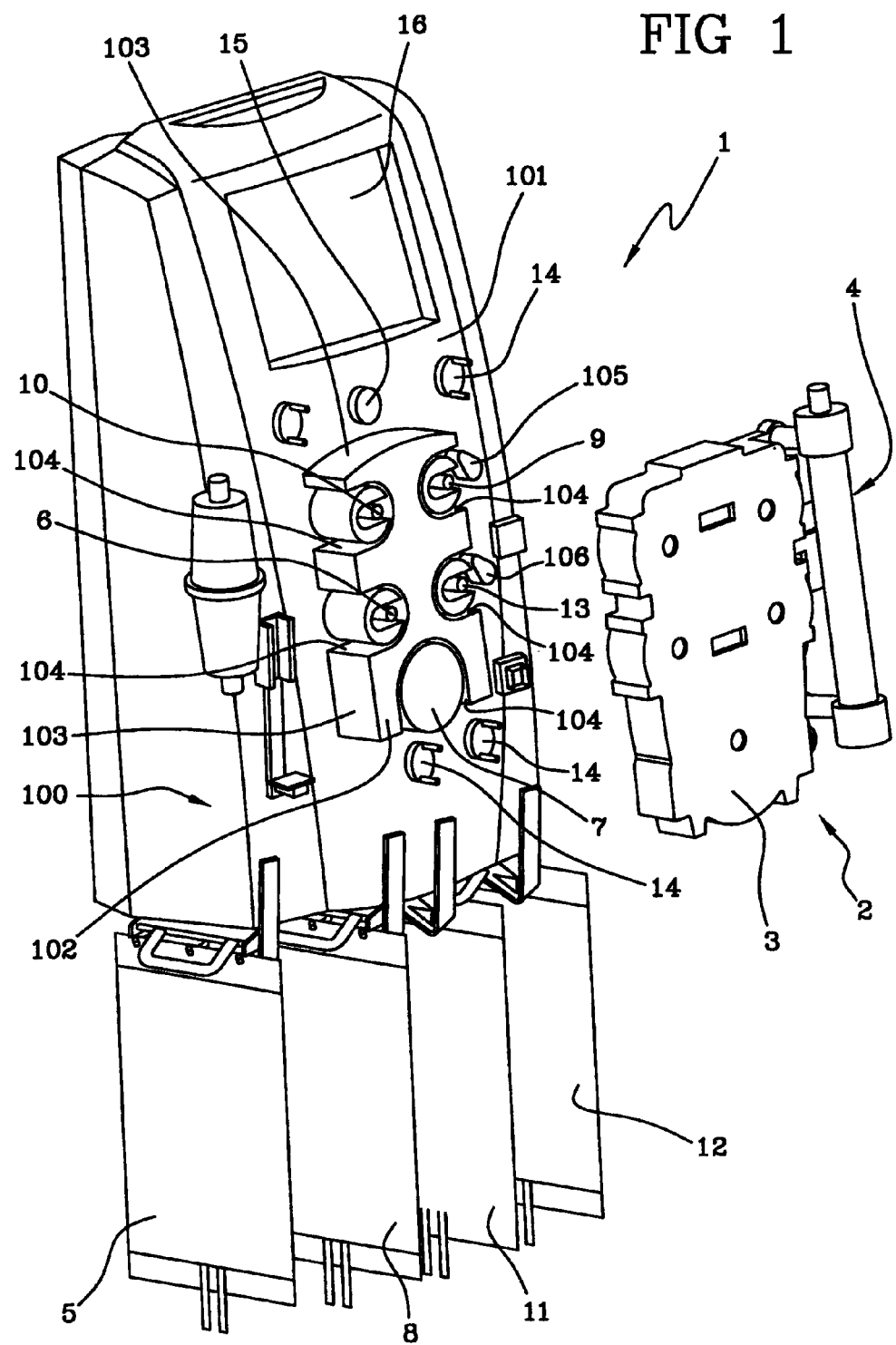
FIG. 1 shows the machine for extracorporeal blood treatment of the invention, to which an integrated module (represented in the figure without associated hydraulic circuit) is associable.

With reference to FIG. 1, 1 denotes in its entirety a machine for extracorporeal blood treatment, represented in the illustrated embodiment by a dialysis machine which is suitable for intensive treatment of acute kidney failure. 2 denotes in its entirety an integrated module which can be coupled to the dialysis machine 1. The integrated module 2 is constituted by a combination of at least one support element 3 of a distribution circuit (of known type and not illustrated) arranged on the support element 3, and a blood treatment unit 4. The blood treatment unit 4 can be, for example, a plasma filter, a hemodialysis filter, a hemofiltration filter, or a different unit.

The hydraulic circuit, which is completed by a combination of the integrated module 2 and the machine 1, comprises a blood circuit which removes blood from a patient, for example via a catheter inserted in a vascular access of the patient, and takes the blood though a blood removal line to the treatment unit 4.

The blood passes through a first chamber (blood chamber) of the treatment unit 4 and, via a return line, is transported back to the patient.

Immediately downstream of the blood removal zone, connection is made between the removal line and an auxiliary pre-infusion line.

In particular, the machine includes at least one container of a first sterile fluid 5 for supplying the pre-infusion line; fluid transport means, in the embodiment constituted by a pre-infusion pump 6, for example a peristaltic pump, control the flow of fluid in the pre-infusion line directly into the blood via a direct connection to the blood removal line.

Generally the container of the first sterile fluid can contain a pre-infusion fluid, although the same container can be used for containing an anticoagulant, usually of a locally-acting type.

The machine further comprises means for transporting fluid, i.e. in the embodiment at least one blood pump 7 for control and management of a correct blood flow in the circuit. The blood pump 7 is peristaltic.

Once a blood circulation direction has been established from the blood removal zone to the blood treatment unit 4, and thereafter to the blood return line towards the patient, a blood pressure sensor is included immediately downstream of the auxiliary pre-infusion line.

Continuing along the blood circulation direction, a device is included for administration of an anticoagulant, for example a syringe containing appropriate doses of heparin.

The blood then crosses a further pressure sensor which monitors the correct flow rate internally of the blood circuit.

After crossing the first blood chamber of the treatment unit 4, where substance-exchange and molecular and fluid exchange takes place through a semi-permeable membrane, the treated blood enters the return line, crossing a gas separator (generally air), where any air bubbles present or introduced the blood during treatment are expelled.

The treated blood exiting from the gas separator (also known as a deaeration chamber) crosses a bubble sensor (also known as an air detector) which checks that these dangerous formations are not present in the treated blood, which is about to be sent back into the blood circuit of the patient.

Immediately downstream of the bubble sensor a closure element is located, which on activation of an alarm can block the blood flow towards the patient.

In particular, if the bubble sensor reveals the presence of anomalies in blood flow, the machine, by means of the closure element (which can be a cock, a clamp or the like) the blood passage would immediately be stopped in order to prevent any kind of consequence to the patient.

Downstream of the closure element the treated blood is returned to the patient undergoing treatment.

The distribution circuitry comprises a first circuit of a second sterile fluid (dialysing liquid) having at least one inlet line to the blood treatment unit 4 and an outlet line from the treatment unit 4.

At least one container of the second sterile fluid 8 is destined to supply the inlet line of the first circuit.

The inlet line is destined to cooperate with means for fluid transport, being at least one pump 9 (in the embodiment a peristaltic pump) predisposed on the frontal part of the machine to control the flow of the second sterile fluid coming from the container 8, and to define a circulation direction.

Downstream of the pump 9 of the second sterile fluid, along the circulation direction, a branch is included which divides the first circuit of the second sterile fluid into an inlet branch and an infusion branch.

In particular the infusion branch is connected to the blood circuit return line. In other words, with this infusion line infusion can be made directly into the blood, using the contents of the container 8 of the second sterile fluid.

The inlet branch takes the second sterile fluid directly to the blood treatment unit 4, in particular to a second chamber (dialysis chamber) of the unit 4.

The first circuit of the second sterile fluid is further associated to a first selector which determines the percentage quantities of fluid flow into the infusion branch and the inlet branch.

Generally the first selector, usually located in proximity of the branch, enables selection between at least a first operative condition, in which the second sterile fluid can pass into the inlet branch but cannot pass into the infusion branch, and a second operative condition, in which they allow passage of fluid into the infusion branch but not into the inlet branch.

In other words the first selector can be constituted by a valve element suitable for operating in a fluid circuit, which can alternatively shut off passage of fluid into one or the other branch. Selectors can be used, if preferred, which can decide prior to starting the quantity of the second sterile fluid which can pass at a same time into one and the other branch. Otherwise the percentage amounts of fluid passing into one branch or the other can be established according to determined times and therapies.

The second sterile fluid (dialysing liquid) crosses the inlet branch and enters the second chamber (dialysis side) of the blood treatment unit 4.

In particular the first chamber (blood chamber), crossed by the blood flow, is separated from the second chamber (dialysis chamber), crossed by the second sterile fluid, by a semi-permeable membrane which enables passage of the damaging molecules and substances and fluids in the blood towards the second sterile fluid (dialysing liquid), mainly through convection and diffusion processes; at the same time, and by the same principles, passage of substances and molecules from the second sterile fluid and towards the blood is allowed.

The second sterile fluid, for dialysis, enters the outlet line of the first circuit and crosses a special pressure sensor for controlling the functioning of the line.

Means for transporting the fluid, for example an effluent drainage pump 10, are present, which control the flow in the fluid circuit outlet line. This pump 10, as the others, is usually peristaltic.

The discharge fluid then crosses a blood leak detector 15 and is sent on to an effluent collection container 11.

An infusion line is located on the return line of the blood circuit. In particular, a third sterile fluid (infusion fluid) is sourced from at least one auxiliary container 12 and, by action of a fluid transport means, generally an infusion pump 13 which controls flow (in the embodiment a peristaltic pump), is sent directly to the blood circuit return line.

The third sterile fluid (infusion liquid) can be sent directly into the gas separator device.

The post-infusion branch of the first circuit of the second sterile fluid and the infusion line of the third sterile fluid are provided with a common terminal inlet tract to the blood circuit.

The terminal inlet tract is located downstream of the infusion pump 13 with respect to an infusion direction, and sends the fluid directly into the gas separator.

At least one pre-infusion branch is present in the infusion line, connected to the blood circuit removal line.

In more detail, there is a branch located downstream of the infusion pump 13 with respect to the infusion direction, which divides the infusion line into a pre-infusion branch and a post-infusion branch.

The pre-infusion branch takes the fluid removed from the container to the blood circuit removal line downstream of the blood pump 7 (downstream with respect to the circulation direction).

The post-infusion branch is directly connected to the common terminal tract.

The infusion line further comprises a second selector for determining the percentage quantities of liquid flow to send into the post-infusion branch and the pre-infusion branch. The second selector, located in proximity of the branch, is positionable between at least one first operative configuration, in which fluid can pass into the pre-infusion branch but not the post-infusion branch, and at least a second operative configuration, in which fluid is allowed to pass into the post-infusion branch and not the pre-infusion branch.

As with the first selector on the first circuit of the second sterile fluid, the second selector is able to establish percentages of fluid passing into each of the two branches, and can if necessary vary the times according to the treatments to be carried out. The first and second selectors are usually, but not necessarily, of similar type.

The machine is provided with means for determining at least the weight of the container of the first sterile fluid 5 and/or the container of the second sterile fluid 8 and/or the container of the third sterile fluid 12 and/or the discharge container 11. The means for determining are constituted by weight sensors, for example scales (at least one independent scales for each container or fluid bag associated to the machine).

There will be at least four of these scales present, each independent of the others, and each predisposed to measure the respective weight of a container 5, 8, 11, 12.

There is also a CPU active on the blood circuit and in particular on the pressure sensor, the blood pump 7, the heparin infusion device, the further pressure sensor, as well as on the bubble sensor and the closure element.

The CPU is also used for controlling the first circuit of the second sterile fluid, and in particular to receive data sent by the scales relating to the weight of the container 8; it is also active on the pump 9, the first selector, the pressure sensor, the drainage pump 10 and the scales weighing the effluent discharge container 11.

The CPU is also active on the infusion line of the third sterile fluid, monitoring the weight of the container 12 (measured by a scales), and also controls the infusion pump 13 and the second selector.

Finally, the CPU is active on the auxiliary line for pre-infusion of the first sterile fluid, measuring the weight of the container 5 via a scales and commanding the pre-infusion pump 6 according to the treatment to be carried out.

The above, purely descriptive, account of the hydraulic circuitry of the machine for extracorporeal blood treatment will now be followed by a brief explanation of how the device functions.

Before the actual treatment begins, the apparatus must be prepared. The whole hydraulic circuitry and the treatment unit are correctly associated to the machine so that the various peristaltic pumps engage the respective tracts of tubing, and all the sensors are correctly positioned; also, the relative bags containing the various fluids are joined up to the respective supply or receiving lines of the liquids, and the blood circuit is connected up to an artery or vein of the patient. When set-up is complete, an initial circulation of the blood internally of the respective circuit is made.

According to the type of treatment selected (pure ultrafiltration, hemodialysis, hemofiltration, hemodiafiltration, etc.), the machine for extracorporeal blood treatment is automatically activated and controlled by the processing unit.

The machine 1 exhibits a machine body 100 provided, on a front surface 101 thereof, with peristaltic pumps 6, 7, 9, 10, 13, destined to cooperate in use with respective tracts of U-shaped tubing on the integrated module.

The machine body 100 exhibits a relief acting as a positioning guide 102 which projects from the front surface 101, which is complementarily shaped with respect to the support element 3 with which it will couple in use.

In other words, the guide 102 exhibits a lateral surface 103 which, when the integrated module is coupled thereto, is contained within a perimeter wall of the support element 3.

The peristaltic pumps also project from the front surface 101 of the machine body 100 and at least a part of the lateral surface of the pumps is complementarily shaped with respect to the perimeter wall of the support element 3.

The projecting peristaltic pumps and the guide 102 in combination define seatings 104 having a semicircular shape, i.e. a U-shape, which seatings 104 are destined to receive the corresponding tracts of U-shaped tubing of the circuitry.

A first mobile element 105 and a second mobile element 106, substantially identical and borne directly on the machine body 100, are destined to be active on the infusion and/or inlet branch of the second sterile fluid (the first mobile element 105) and, respectively, on the pre-infusion branch and/or the post-infusion branch of the third sterile fluid (the second mobile element 106). In particular the first and second selectors can be constituted by the mobile elements 105, 106, destined to be controlled by the CPU to selectively allow or block passage of fluid into one or another of the branches.

The front surface of the machine further exhibits a plurality of fastening elements 14 for fixing the pressure sensors; the pressure sensors associated to the circuitry of the integrated module are hereat connected up to the CPU.

The blood leak detector 15 is also predisposed on the front surface of the machine, and during the apparatus readying stage is associated to the fluid circuit in outlet from the treatment unit 4.

16 denotes a screen, which is part of the machine user interface.

The user interface comprises a touch screen and a controller programmed to display on the screen 16 of the touchscreen a plurality of displays in which the screen 16 is divided into two distinct areas, in which a first area 161 (on the left in the figure) exhibits a plurality of touch keys 17, and a second area 162 (on the right in the figure), by the side of the first area, selectively displays a plurality of pictographs 18, each of which is associated to one of the touch-keys 17.

In the present description, the term "touch screen" refers to a device having a screen for data output, which is also used for input through selection of parts (touch keys) of the screened display using the fingers; the device is able to detect where a user has touched the screen and from this derive the selected commands and perform them.

In figures from 2 to 9 a series of displays are illustrated which relate to a specific series of procedural steps necessary for readying the dialysis apparatus, in particular the procedural steps for mounting the disposable set on the dialysis machine, in relation to a hemodiafiltration treatment.

Figure 2:
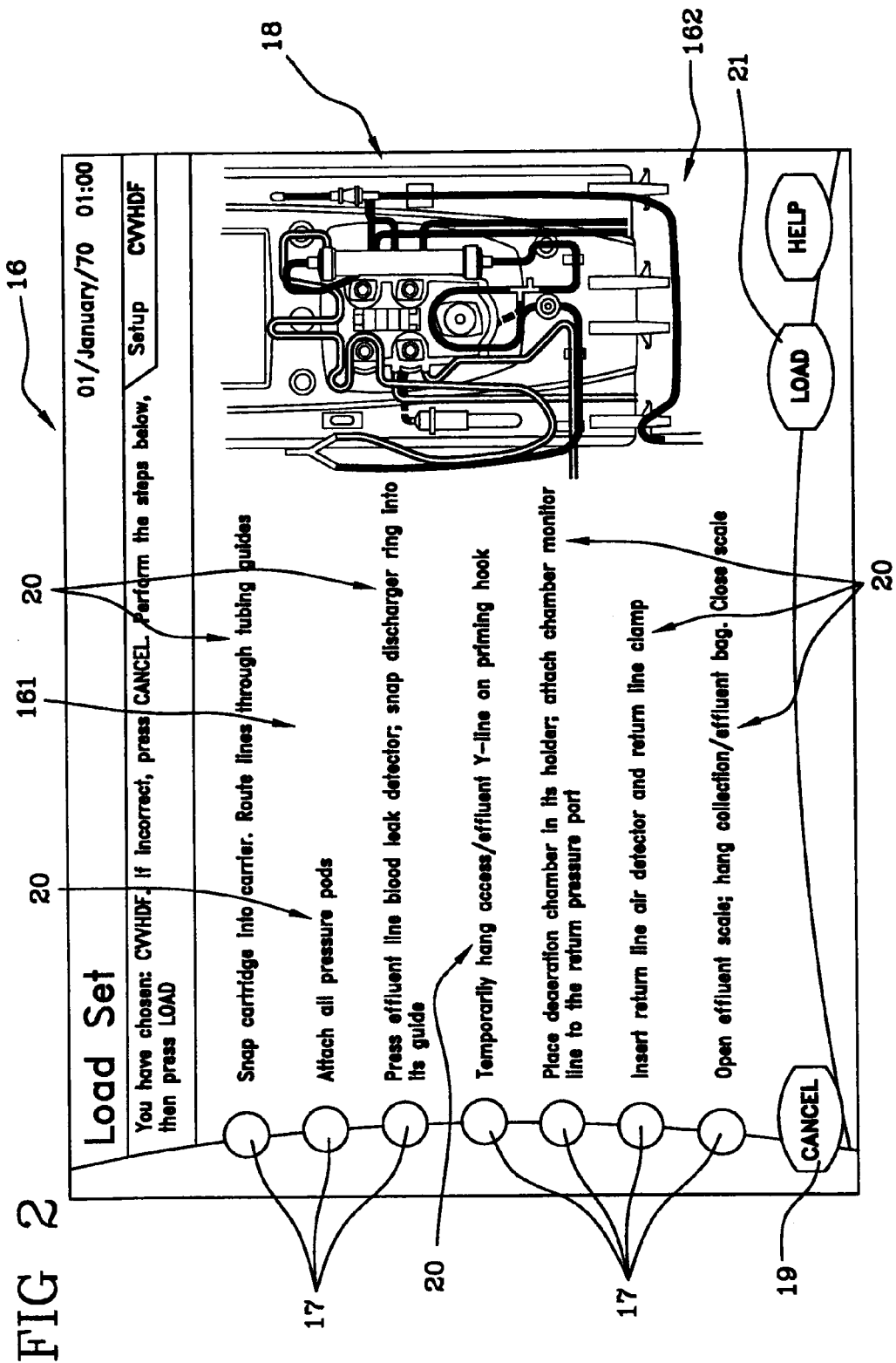

After the operator has used the touch-screen to select the desired treatment (in the illustrated case hemodiafiltration, but which could variously be hemofiltration, hemodialysis, ultrafiltration, plasma exchange therapy etc.), the controller of the user interface is programmed to bring up on-screen the display of FIG. 2, in which the indications relating to the steps the operator must perform to prepare the machine are shown. In this case the activity consists in mounting the disposable set, where the set comprises, as mentioned above, the support element 4 and relative circuitry, and the blood treatment unit 5. The data appearing on-screen comprises, in the example, an English expression viz "Load set", which is an instruction relating to the next steps to take.

The display also includes an indication of the selected treatment. In this case the treatment selected is hemodiafiltration, and the well-known English acronym for this is "CVVHDF".

The display comprises a touch key 19 for cancelling the treatment selection, if the operator judges it to be incorrect.

The touch keys 17 correspond to one or more procedural steps, arranged in top-down order according to temporal sequence for carrying out the steps necessary for loading a disposable set on the machine.

The first area 161 of the display has, by the side of each touch key 17, an alphanumeric indication or is legend 20 describing in word form the procedural step or steps the operator must perform that are associated with the respective touch key 17.

A pictograph 18 appears in the second area 162 of the screen in this display, which pictograph 18 represents the front of the dialysis machine, with the disposable set already mounted on the machine. The pictograph 18 (FIG. 2) describes the fluid distribution circuitry using lines in colour code according to the type of fluid line represented, so that, for example, the blood removal line is represented by a red line, the blood return line is blue, the auxiliary pre-infusion line of the first sterile fluid is white, and so on.

On touching any one of the touch keys 17 the controller brings up a pictograph 18 in the second area of the display, corresponding to the instruction associated to the selected touch key 17.

As can be seen in figures from 2 to 9, each pictograph represents the machine for extracorporeal blood treatment and at least a part of the disposable element operatively associated to the machine.

Figure 3:
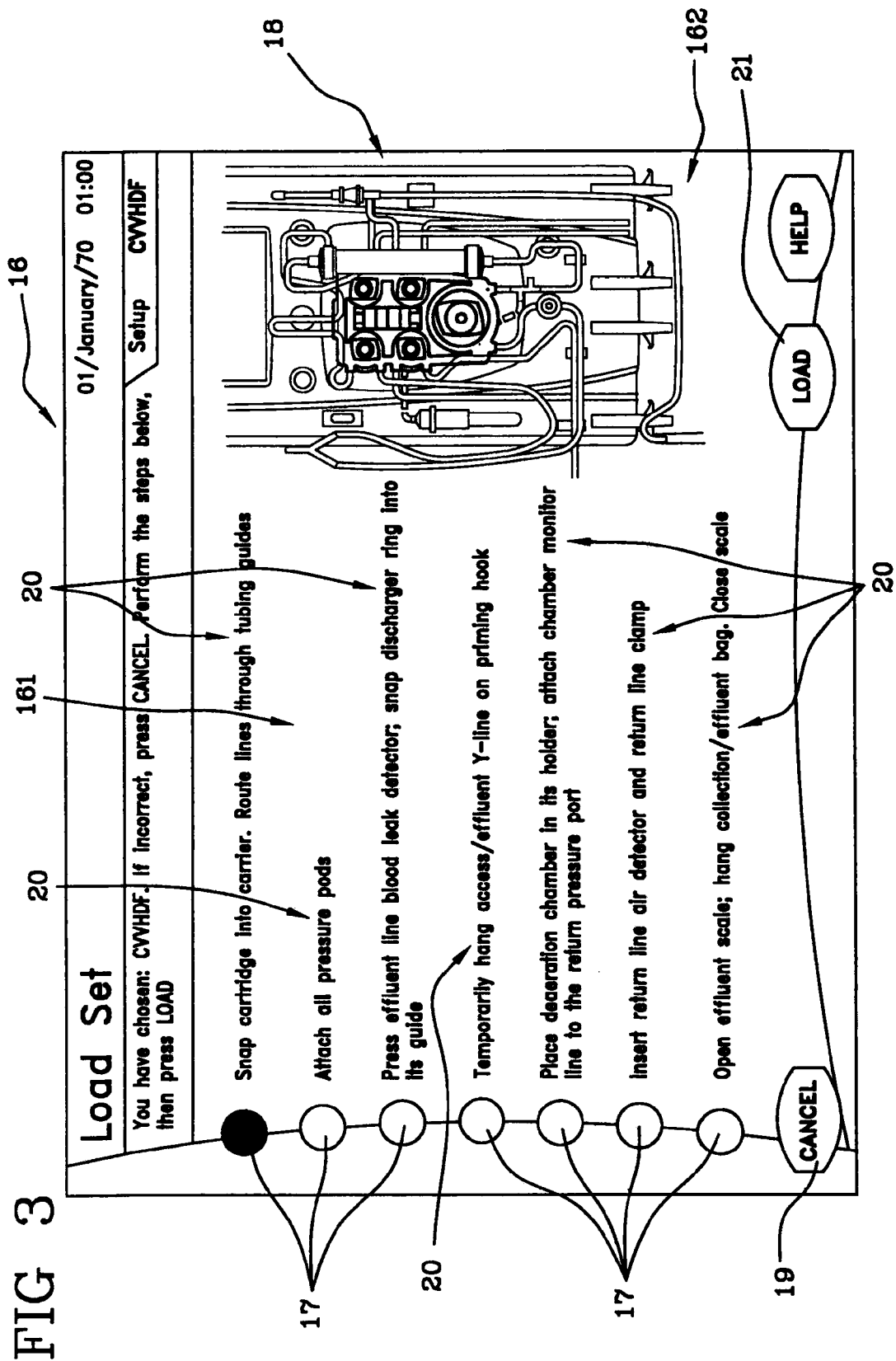

FIG. 3 shows the display which appears on selection of the first touch key 17 giving the instructions for fixing the integrated module 2 in the special seating predisposed on the front of the machine, and for engaging the various fluid lines in the respective guides, also located on the front of the machine.

Selecting the first key (at the top of the display) produces the following changes to the display: firstly the pictograph 18 (FIG. 3) which appears in the second area 162 exhibits an illustration of the machine front, with an accentuation of the support element 3 of the integrated module in work position; secondly the touch key 17 selected changes appearance (for example it is more luminous or changes colour) with respect to the other touch keys, so that the operator is reminded of which touch key 17 (and therefore which operational instruction) the pictograph 18 in the second area 162 of the display is associated to. There are other ways in which the pictograph 18 in the second area 162 can be associated to the corresponding data or legend shown in the first area 161; for example the legend could be colour-coded to distinguish it from the other writing on the screen, or the selected touch key 17 could begin to flash, or similar.

Figure 4:
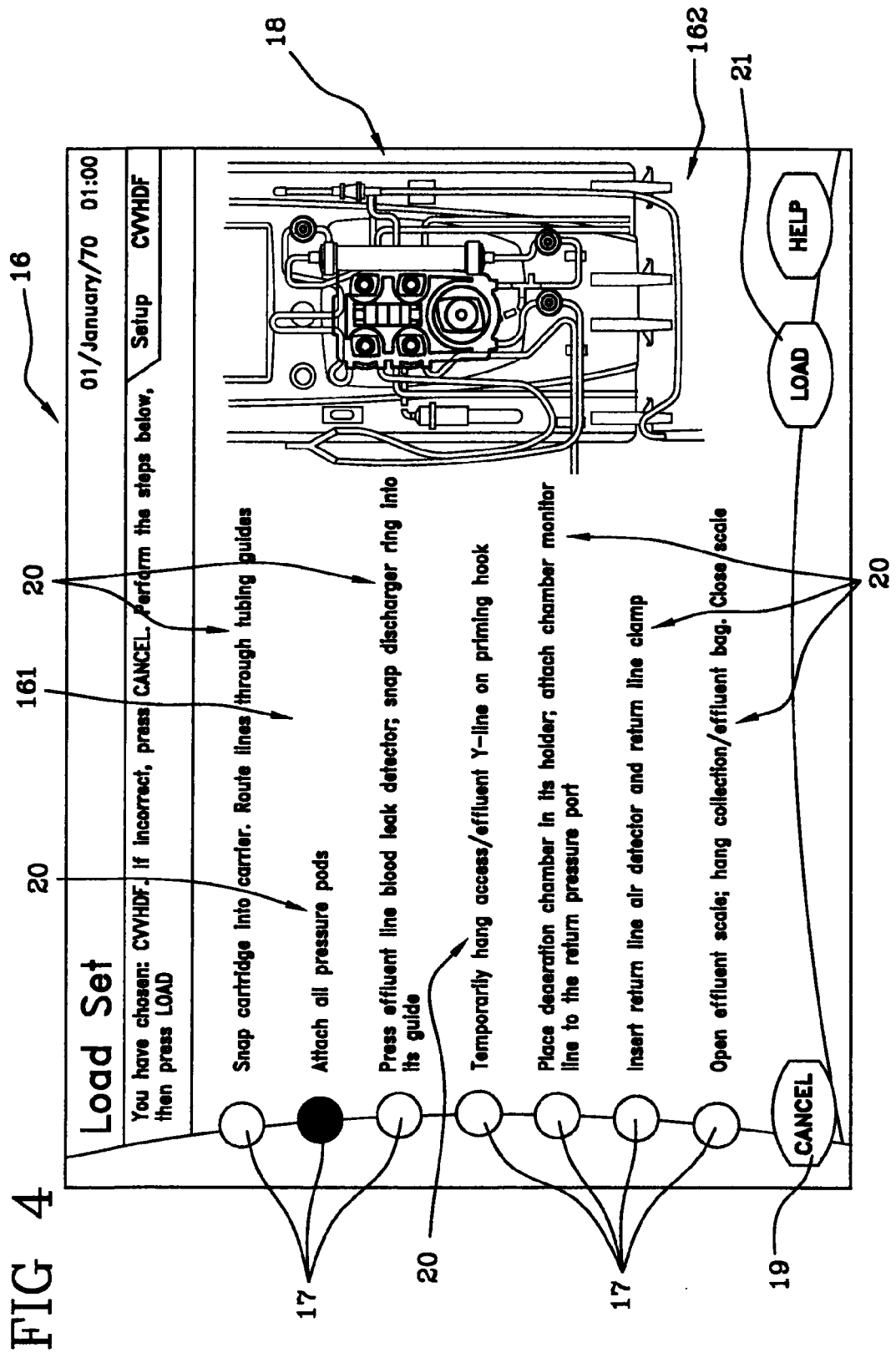

FIG. 4 shows the display which appears by effect of selecting the second touch key 17 from the top of the display. This touch key 17 is associated to the instruction to apply the pressure sensors (or pods) to the corresponding fastening elements 14 predisposed on the front of the machine. The corresponding pictograph 18 (FIG. 4) which appears in the second area 162 of the screen represents the front of the machine, with the pressure sensors highlighted in the work position, coupled to the relative fastening elements 14. In this case too the selected touch key 17 is in some way distinguished vis-à-vis the other touch keys 17.

Figure 5:
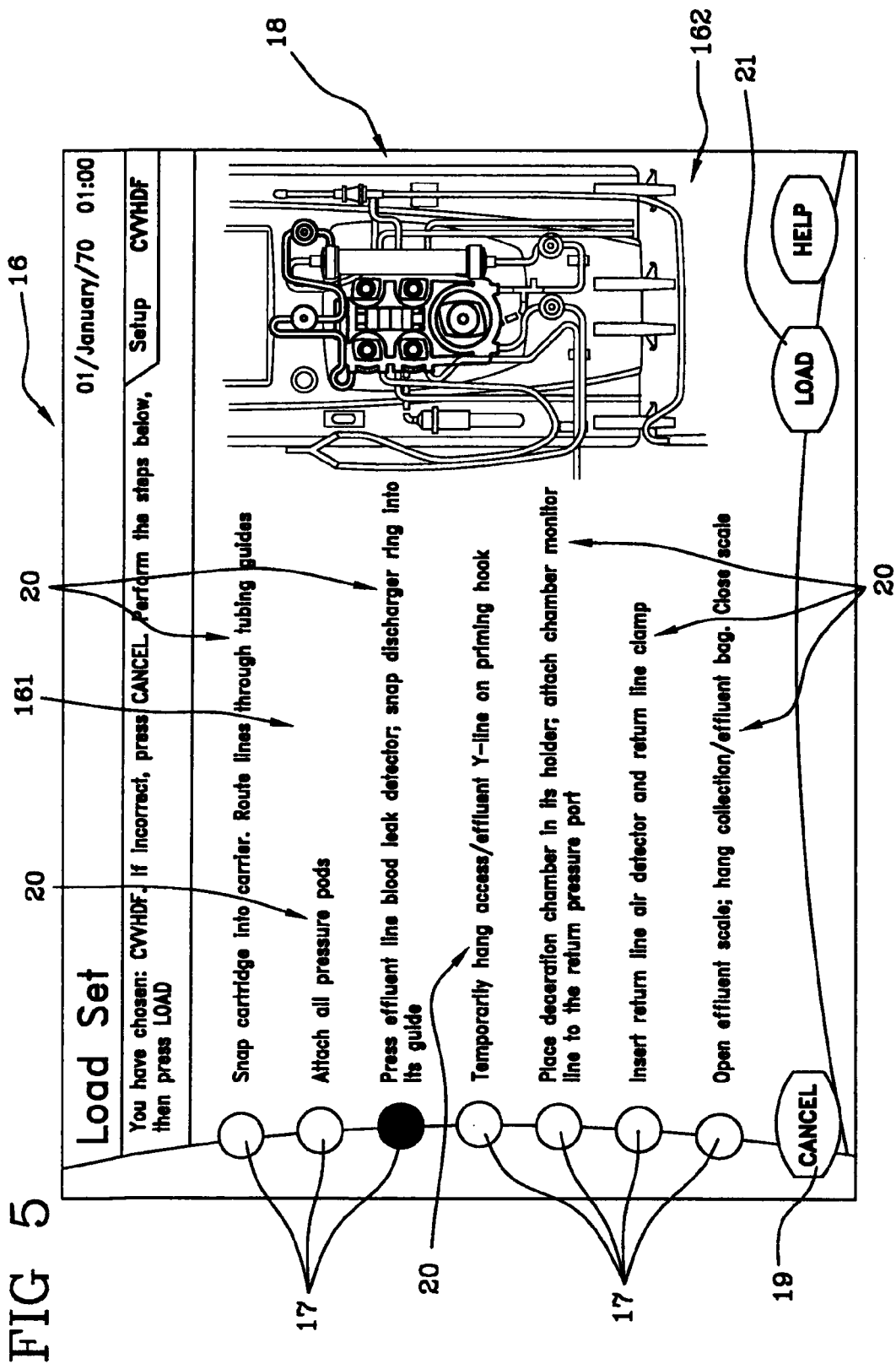

FIG. 5 shows the display that appears on selection of the third touch key 17 from the top. This third touch key 17, which as before with other keys is in some way differentiated from the other keys, is associated to the instruction to operatively connect the outlet line for used fluid exiting the blood treatment unit (where the effluent dialysis fluid flows, also known as the discharge line) with the blood leak detector 15 predisposed on the front of the machine. In the pictograph 18 (FIG. 5) which appears by selection of the third touch key 17, and which schematically illustrates the front of the machine, the above-cited outlet line and the blood leak detector 15 are particularly highlighted. Visual accentuation, in this case as in the following cases, can be achieved in any known way, for example by greater luminosity of the part to be highlighted with regard to the rest.

Figure 6:
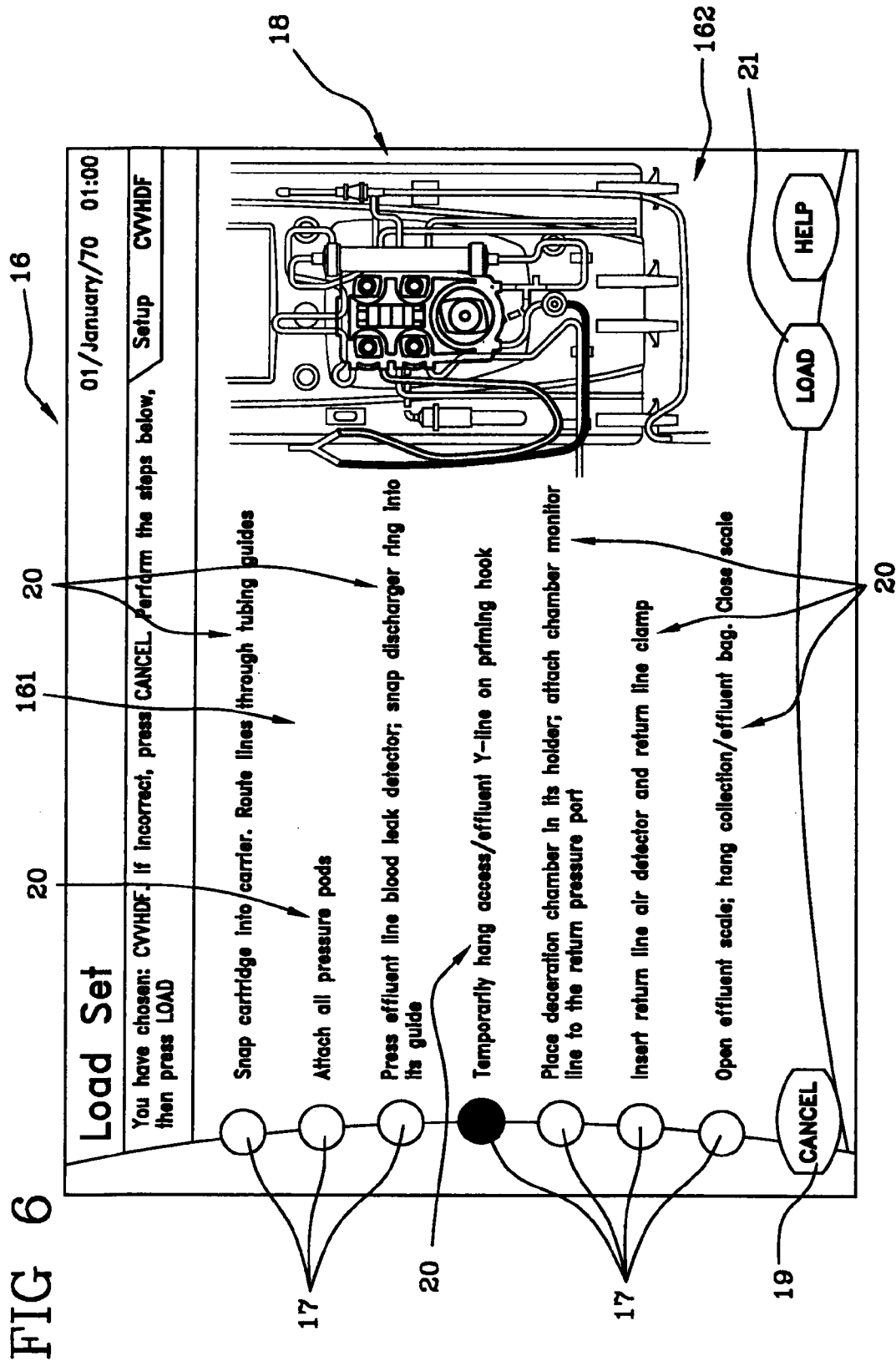

FIG. 6 shows the display that appears when the fourth touch key 17 from the top is selected. This touch key 17 is associated to the instruction for temporarily hanging one or more lines, in the embodiment the blood removal line and the discharge fluid line, to a support element provided on the machine, in preparation for a priming operation which will follow on from the mounting operation of the disposable set on the machine. In this case too the operator is assisted in the machine preparation, thanks to the fact that after having selected the touch key 17 relating to the instruction to be carried out, the operator finds, in the second area 162 of the screen, a graphic illustration of the same instruction, constituted by a pictograph 18.

In the first area 161 of the screen display the operator has an overview of the various operations to be carried out to complete the mounting procedure for the disposable set on the machine; but the operator can also receive further data, displayed on-screen in the second area 162 thereof, which relate to each single instruction or group of instructions described in the first part 161 of the screen and selected as required. The written data (legends 20), remains visible at all times to the operator no matter which touch key 17 is selected, while the data displayed on-screen in the second area 162 of the display change according to which touch key 17 is selected time-by-time by the operator. The further and more specific data relating to each touch key 17 and displayed in the second area 162 of the screen takes the form of pictographs 18 represented by the operations the operator is to carry out on the machine.

Figure 7:
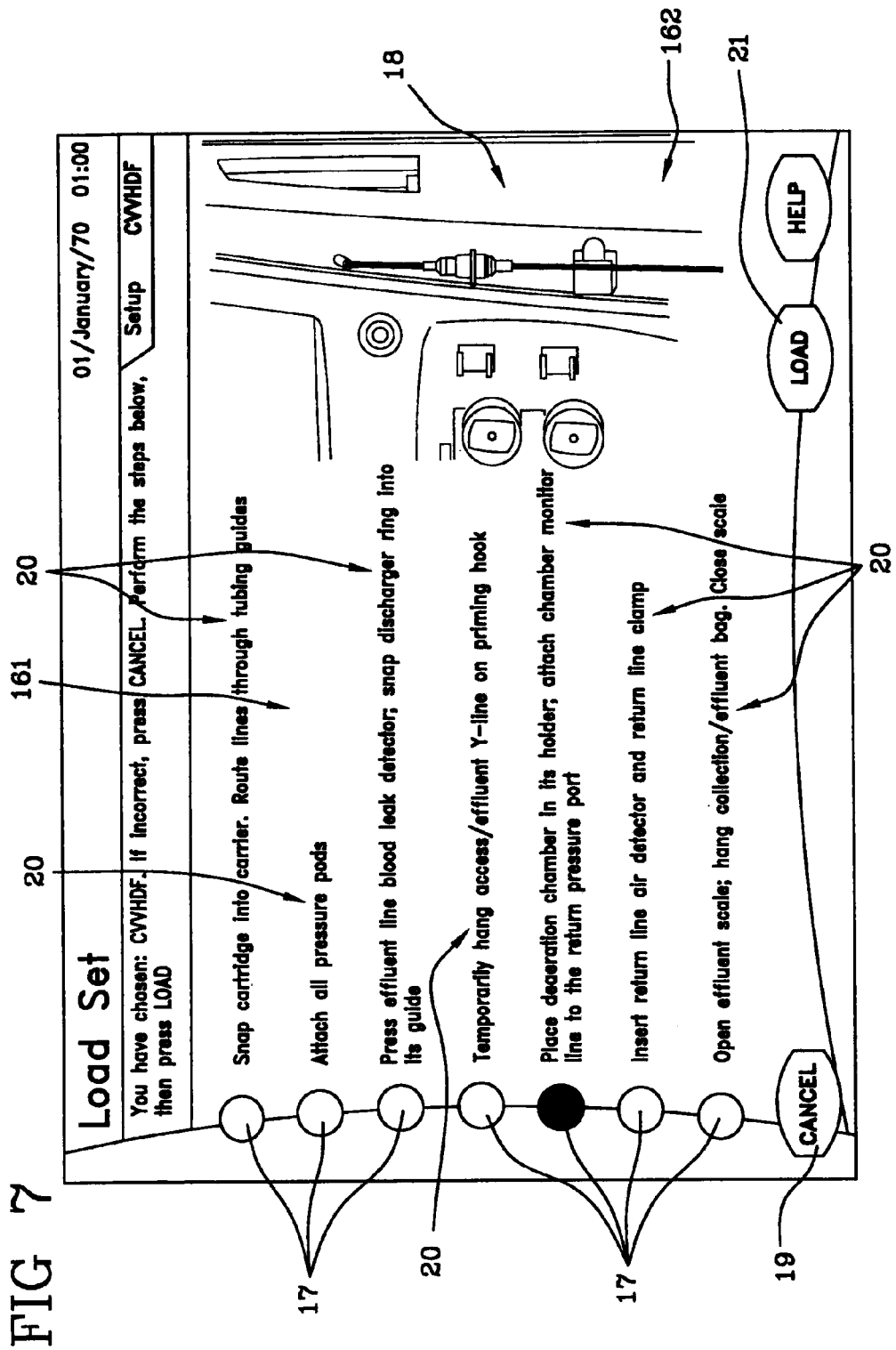

FIG. 7 shows the display that appears on-screen on selection of the fifth touch key 17. The data (or data group) associated to the fifth touch key 17 is related to positioning the gas separator device in the special support element predisposed on the front of the machine, and to connect up an auxiliary line for the pressure connection, which exits from the top of the chamber itself, to an inlet port, also predisposed on the front of the machine, for sending the pressure in the chamber to a pressure transducer inside the machine. Also in the present case the pictograph 18 (FIG. 7) appearing on the second area 162 of screen is descriptive of the above-cited instruction.

Figure 8:
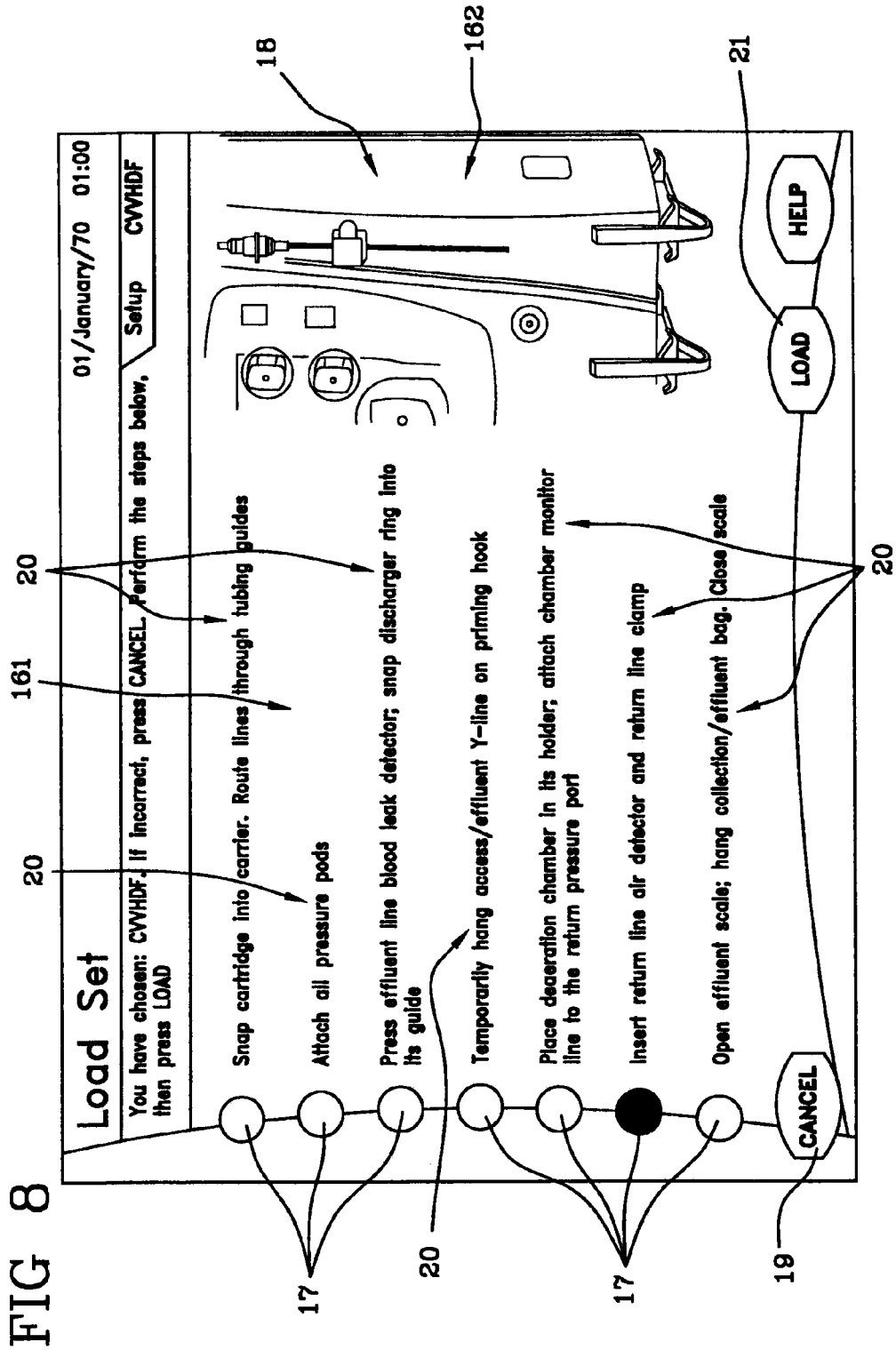

FIG. 8 is the display that appears on selection of the sixth touch key 17, to which are associated the instructions for connecting the blood return line to the bubble sensor, and closing the line. As with the previous displays, the pictograph 18 which appears in the second area 162 of the screen describes the instruction given.

FIG. 9 shows the display which appears when the seventh touch key 17 is selected, containing the instructions for activating the scales of the discharge container of the used liquid, and for hanging the (empty) effluent collection container 11 on the special support hook therefor; and thereafter, for deactivating the scales. The pictograph 18 which appears on the right of the screen is illustrative of the above-described group of instructions.

Once all the instructions have been carried out, the operator presses another touch key 21 located in a lower region of the display, to continue the dialogue with the machine control unit in order to set up the machine correctly for the treatment required.

The touch screen controller is thus programmed to selectively display a plurality of images (pictograms 18) on the second area 162 of the screen; selection of one of the touch keys 17 brings on-screen an image which is dedicated only to the selected touch key 17.

The controller is also programmed so that the various images shown on the second part of the display 162 appear alternatively and not contemporaneously.

The controller is programmed so that the various images are at least partly different to each other, due to the fact that they describe information which is also different in each case.

The touch screen comprises a memory containing the above-mentioned data relating to the machine. The controller is programmed so that the various on-screen displays, associated to a same series of procedural steps (for example the series of procedural steps for mounting a disposable set for a hemodiafiltration treatment, as in the illustrated embodiment, or for priming the disposable set, or for preparing and connecting the containers 8, 11, 12 of the various sterile liquids to the apparatus, or for connecting up the patient to the apparatus, and so on), each comprise a display including the relevant data (for example by displaying a button-like touch key next to a legend explaining the information, or by writing the data in an area of the screen which functions as a touch key, or in some other way).

The controller can be programmed, as in the illustrated example, so that, by effect of activation of any one of the various touch keys 17, the data displayed cannot be cancelled and is therefore still visible in the first area 161 of the screen.

As has been explained, the data comprises instructions for readying the machine. The user interface is programmed so that it visualizes images which can be pictographs representing configurations of the machine, in which the configurations are correlated to the instructions given.

The resolution of the second area 162 of the display, which is destined to display the pictographs, is at least 80 pixels per inch. In the illustrated embodiment, in which the touch-screen is 12 inches with 800×600 pixel, the resolution of the second area 162 of the screen, which is destined to show the pictographs and which occupies an area of 250×405 pixel, is about 83 pixels per inch.

The touch screen controller is programmed so that each of the above-mentioned images, displayed in the second area 162 of the screen, is not active in the user-display dialogue process, i.e. there is no interaction on the part of the user using the second area 162 of the screen, which is destined, in the displays relating to the preparation procedure of the machine, to offer only image visualization, with no touch keys or other possibilities of activation on the part of the operator, who is essentially passive as regards what happens in the second area 162, being able only to view the images.

As has been described, the controller is programmed so that by activation of any one of the touch keys, a part of the first area 161, visually associated to the activated touch key, undergoes a change. In the illustrated embodiment the change consists in a change of colour in the "button" representation of the touch key on-screen.

The controller is also programmed not to enable any change of the contents of the above-described data by a user operating the touch screen. The contents of the data can be modified only by an operator who is also an expert in electronics and who is therefore able to intervene in the machine operating system. The nature of the data (for example, operative instructions for readying the machine) is such that there are no variable and settable parameters (as might be the case with the treatment parameters, such as for example the blood flow rate, the duration of treatment, the quantity of fluid to be removed from the patient, and so on).

In a further embodiment of the invention, not illustrated, the user interface controller is programmed to visually modify at least one area of the display by effect of carrying out at least one of the above-described operating instructions. In particular, the part of display which is modified is logically connected to the instruction given, and the change in the area of display assumes the guise of a response by the machine to the operator, subsequent to an operating instruction's having been correctly performed. For example, the response that appears on-screen when the operation has been correctly carried out might consist in highlighting, or colour-coding, or flashing etc. either the part of the pictograph which represents the part of the disposable set related to the instruction just carried out, or the alphanumeric image which appears on-screen in the first area 161 and which describes the instruction which has just been carried out, or both the areas of the display. This signal for indicating a correct carrying-out of the instruction can last for a predetermined time, or, for example, could cease when the operator presses one of the touch keys 17, 19, 21.

The invention claimed is:

1. A machine for extracorporeal blood treatment, comprising:
at least one blood pump;
at least one housing zone configured for receiving a disposable element comprising at least one extracorporeal blood circuit in a position wherein the at least one extracorporeal blood circuit is operatively associated with the blood pump;
at least one user interface comprising:
at least one touch screen; and
at least one memory containing at least:
a first data item comprising a first operating instruction, the first operating instruction comprising an alphanumeric indication describing in word form how to perform a procedural step to prepare the machine for use,
a second data item comprising a second operating instruction, the second operating instruction comprising an alphanumeric indication describing in word form how to perform a procedural step to prepare the machine for use,
a first image comprising a first pictograph of the machine in a first configuration correlated to said first operating instruction to illustrate in graphical form how to perform the procedural step to prepare the machine for use provided by said first operating instruction, said first pictograph comprising a schematic representation of the front of the machine and of the disposable element to be operatively associated to the machine and visually accentuating at least a first part of said disposable element,
a second image comprising a second pictograph of the machine in a second configuration correlated to said second operating instruction to illustrate in graphical form how to perform the procedural step to prepare the machine for use provided by said second operating instruction, said second pictograph comprising a schematic representation of the front of the machine and of the disposable element to be operatively associated to the machine and visually accentuating at least a second part of said disposable element different from said first part; and
at least a processor configured to:
display at least one display on a screen of said touch screen, said at least one display including at least a first area and a second area, said first area being distinct from said second area, said first area exhibiting at least a first touch key and a second touch key;
display said first data item and said second data item on said first area, said first data item being displayed in a visually-associated position to said first touch key, said second data item being displayed in a visually-associated position to said second touch key, said first touch key, second touch key, first data item and second data item being displayed contemporaneously on said first area;
detect activation of said first touch key and said second touch key; and
display said first image or said second image on said second area, said first image being displayed on said second area when said first touch key is activated, said second image replacing said first image on said second area such that said second image is displayed on said second area in place of said first image when said second touch key is activated.

2. The machine of claim 1, wherein the memory includes more than two data items each comprising a respective operating instruction, each respective operating instruction comprising an alphanumeric indication describing in word form how to perform a procedural step to prepare the machine for use, and wherein the processor is configured to:
display in the first area more than two touch keys each having the respective data item displayed in a visually-associated position, and
contemporaneously display all said data items on said first area providing indications relating to the steps the operator must perform to prepare the machine before the treatment begins.

3. The machine of claim 1, wherein the processor is configured to detect activation of anyone of said touch keys and display a respective image on said second area when the corresponding touch key is activated.

4. A machine according to claim 1, wherein the processor is configured to display and to keep displayed said first and second data items on said first area following activation of any one of the first and second touch keys.

5. A machine according to claim 1, wherein the processor is configured to display said first and second touch keys on said first area following activation of any one of the first and second touch keys.

6. A machine according to claim 1, wherein the processor is configured to prevent any change of contents of the plurality of data via the touch screen on the part of an operator.

7. A machine according to claim 1, wherein the processor is configured to have the second area of the display without areas predisposed for data input, at least in areas containing the at least two images.

8. A machine according to claim 1, wherein the machine is predisposed to perform at least one of the following extracorporeal treatments: hemodialysis, hemofiltration, hemodiafiltration, pure ultrafiltration, therapeutic plasma exchange, hemoperfusion.

9. The machine of claim 1, wherein the processor is configured to visually modify a part of the first area by effect of an activation of anyone of the at least two touch keys, the part being visually associated to the activated touch key.

10. A machine according to claim 1, further comprising at least one sensor for detecting proper positioning of a part of the disposable item, and wherein the processor is configured to detect whether the part of the disposable item related to an operating instruction has been properly positioned and, when the processor detects proper positioning of said part, said processor is configured to visually accentuate one selected in the group comprising:
- the data item describing the instruction that has just been carried out,
- the image corresponding to the instruction that has just been carried out, and
- both the image and the data item corresponding to the instruction that has just been carried out.

11. A machine according to claim 10, wherein the processor is configured to keep said visual accentuation for a predetermined time, or until detection of a pressing of one of the touch keys.

* * * * *